United States Patent
Deitcher et al.

(10) Patent No.: US 11,273,179 B2
(45) Date of Patent: Mar. 15, 2022

(54) METHODS FOR TREATING NON-CANCEROUS DISORDERS USING HEMATOPOIETIC CELLS

(71) Applicant: MEDEOR THERAPEUTICS, INC., South San Francisco, CA (US)

(72) Inventors: Steven R. Deitcher, San Mateo, CA (US); Corinna X. Chen, South San Francisco, CA (US)

(73) Assignee: MEDEOR THERAPEUTICS, INC., South San Francisco, CA (US)

( * ) Notice: Subject to any disclaimer, the term of this patent is extended or adjusted under 35 U.S.C. 154(b) by 369 days.

(21) Appl. No.: 16/351,047

(22) Filed: Mar. 12, 2019

(65) Prior Publication Data

US 2019/0275085 A1    Sep. 12, 2019

Related U.S. Application Data

(60) Provisional application No. 62/641,757, filed on Mar. 12, 2018.

(51) Int. Cl.
*A61K 35/28* (2015.01)
*A61K 35/17* (2015.01)
*A61K 9/00* (2006.01)

(52) U.S. Cl.
CPC ............ *A61K 35/17* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 5,607,579 A | 3/1997 | Latham, Jr. et al. | |
| 5,876,708 A | 3/1999 | Sachs | |
| 6,280,957 B1 | 8/2001 | Sayegh et al. | |
| 6,544,506 B2 | 4/2003 | Reisner | |
| 6,558,662 B2 | 5/2003 | Sykes et al. | |
| 6,743,192 B1 | 6/2004 | Sakota et al. | |
| 6,877,514 B2 | 4/2005 | Sykes | |
| 7,270,810 B2 | 9/2007 | Reisner et al. | |
| 7,288,255 B1 | 10/2007 | Shlomchik et al. | |
| 7,297,329 B2 | 11/2007 | Akashi et al. | |
| 7,332,157 B2 | 2/2008 | Sykes | |
| 7,638,121 B2 | 12/2009 | Sykes | |
| 7,776,591 B2 | 8/2010 | Xia et al. | |
| 7,811,815 B2 | 10/2010 | Brown | |
| 7,939,062 B2 | 5/2011 | Sykes | |
| 8,734,786 B2 | 5/2014 | Miller et al. | |
| 8,916,147 B2 | 12/2014 | Reisner | |
| 8,980,329 B2 | 3/2015 | Brown | |
| 9,090,871 B2 | 7/2015 | Durrant et al. | |
| 9,364,600 B2 | 6/2016 | Pages et al. | |
| 9,452,184 B2 | 9/2016 | Ildstad et al. | |
| 9,504,717 B2 | 11/2016 | Strober et al. | |
| 9,545,427 B2 | 1/2017 | Brown | |
| 9,561,253 B2 | 2/2017 | Strober et al. | |
| 9,695,394 B1 | 7/2017 | Coelho et al. | |
| 2002/0107469 A1 | 8/2002 | Bolan et al. | |
| 2008/0199949 A1 | 8/2008 | Alroy | |
| 2010/0042015 A1 | 2/2010 | Brown | |
| 2010/0310588 A1 | 12/2010 | Bluestone et al. | |
| 2011/0110909 A1 | 5/2011 | Ildstad et al. | |
| 2012/0177621 A1 | 7/2012 | Strober et al. | |
| 2012/0329668 A1 | 12/2012 | Sarwal et al. | |
| 2014/0004085 A1* | 1/2014 | Kaplan | G01N 33/53 424/93.7 |
| 2014/0369974 A1 | 12/2014 | Reisner et al. | |
| 2017/0106086 A1 | 4/2017 | Strober et al. | |
| 2018/0221410 A1* | 8/2018 | Strober | A61K 45/06 |
| 2019/0307803 A1 | 10/2019 | Deitcher | |
| 2019/0358269 A1* | 11/2019 | Reisner | A61K 35/36 |

FOREIGN PATENT DOCUMENTS

| | | |
|---|---|---|
| EP | 2606120 B1 | 10/2015 |
| WO | 1995003062 A1 | 2/1995 |
| WO | 2002040640 A2 | 5/2002 |
| WO | 2003012060 A2 | 2/2003 |
| WO | 2011068829 A1 | 6/2011 |
| WO | 2012024427 A2 | 2/2012 |
| WO | 2012096974 A1 | 7/2012 |
| WO | 2013093919 A2 | 6/2013 |
| WO | 2014133729 A1 | 9/2014 |
| WO | 2017/005647 A1 | 1/2017 |

OTHER PUBLICATIONS

Kalwak K. et al. Higher CD34+ and CD3+ Cell Doses . . . Biol Blood Marrow Transplant 16:1388-1401, 2010. (Year: 2010).*
Ispzua A. et al. The Number of Donor CD3+ Cells is the Most Important Factor . . . Blood 97(2)383-387 2001. (Year: 2001).*
Alexander, 2008, Chimerism and Tolerance in a Recipient of a Deceased-Donor Liver Transplant, N Engl J Med, 358:369-74.
Arai, 2015, Increasing Incidence of Chronic Graft-versus-Host Disease in Allogeneic Transplantation: A Report from the Center for International Blood and Marrow Transplant Research, Biol Blood Marrow Transplant, 21:266-274.
Arbab, 2004, Efficient Magnetic Cell Labeling with Protamine Sulfate Complexed to Ferumoxides for Cellular MRI Blood, American Soc. of Hematology, 104(4): 1217-1223.
Bakhuraysah, 2016, Hematopoietic stem cell transplantation for multiple sclerosis: is it a clinical reality? Sem Cell Res Ther. 2016; 7:12, 12 pages.

(Continued)

*Primary Examiner* — Ralph J Gitomer
(74) *Attorney, Agent, or Firm* — Brown Rudnick LLP

(57) ABSTRACT

The invention provides methods of treating non-cancerous disorders in a subject by providing the subject with compositions containing hematopoietic cells. In certain embodiments, the compositions include CD34+ cells and CD3+ cells. In certain embodiments, the compositions include CD34+ cells and facilitating cells. The methods are useful for treating blood cell disorders and other disorders that can be ameliorated by providing donor hematopoietic cells.

22 Claims, No Drawings

(56) References Cited

OTHER PUBLICATIONS

Beelen, 2000, Transplantation of highly purified HLA-identical sibling donor peripheral blood CD34+ cells without prophylactic post-transplant immunosuppression in adult patients with first chronic phase chronic myeloid leukemia: results of a phase II study, Bone Marrow Transplantation, 823-829, 26, Macmillan Publishers Ltd., Basingstoke, United Kingdom.

Dick, 1997, Assay of human stem cells by repopulation of NOD/SCID mice, Stem Cells, 1997;15 Suppl 1:199-203.

Field, 2001, Tolerance, mixed chimerism and protection against graft-versus-host disease after total lymphoid irradiation, Phil. Trans. R. Soc. Lond. B, 356:739-748.

Frisch, 2014, Hematopoietic Stem Cell Cultures and Assays, Methods Mol Biol. 2014; 1130: 315-324.

Fudaba, 2006, Myeloma Responses and Tolerance Following Combined Kidney and Nonmyeloablative Marrow Transplantation: In Vivo and In Vitro Analyses, American Journal of Transplantation, 6: 2121-2133.

International Search Report and Written Opinion for International Application No. PCT/US2019/025958, filed Apr. 5, 2019, dated Jul. 2, 2019, 7 pages.

International Search Report and Written Opinion for International Application No. PCT/US2019/051711, filed Sep. 18, 2019, dated Jan. 15, 2020, 9 pages.

Jun. 2007, Adoptive T cell therapy for cancer in clinic, J Clin Invest, 117(6):1466-76, vol. 117.

Kalwak, 2010, Higher CD34+ and CD3+ Cell Doses in the Graft Promote Long-Term Survival, and Have No Impact in the Incidence of Severe Acute or Chronic Graft-versus-Host Disease after In Vivo T Cell-Depleted Unrelated Donor Hematopoietic Stem Cell Transplantation in Children, Biol Blood Marrow Transplant, 16:1388-1401.

Kawai, 2008, HLA-mismatched Renal Transplantation without Maintenance Immunosuppression, New England Journal of Medicine, 358(4):353-361.

Khalil, 2017, Rubbing Against Blood Clots Uding Helical Robots: Modeling and In Vitro Experimental Validation, IEEE Robotics and Automation Letter vol. 2, No. 2, 927-934.

Kohrt, 2009, TLI and ATG Conditioning with Low Risk of Graft-Versus-Host Disease Retains Antitumor Reactions after Allogeneic Hematopoietic Cell Transplantation from Related and Unrelated Donors, Blood, 114(5):1099-1109.

Ledford, 2008, Organ Transplant without Rejection, Nature News, ISSN 0028-0836, EISSN 1476-4687 (3 pages).

Leventhal, 2012, Chimerism and tolerance without GVHD or engraftment syndrome in HLA-mismatched combined kidney and hematopoietic stem cell transplantation, Sci Transl Med. 4(124):1-22.

Leventhal, 2013, Tolerance Induction in HLA Disparate Living Donor Kidney Transplantation by Donor Stem Cell Infusion: durable chimerism predicts outcome, Transplantation, 95(1):169-176.

Mali, 2013, Delivery systems for gene therapy, Indian J Hum Genet. Jan.-Mar. 2013; 19(1): 3-8, 8 pages.

Millan, 2002, Mixed chimerism and immunosuppressive drug withdrawal after HLA-mismatched kidney and hematopoietic progenitor transplantation, Transplantation, 73:1386-1391.

Ng, 2009, Isolation of human and mouse hematopoietic stem cells, Methods Mol Biol., 506:13-21.

Perez-Pujol, 2005, Proteomic analysis of gray platelet syndrome by iTRAQ Labelling and mass spetroscopy: a potential new diagnostic strategy for platelet disorders, Blood, (ASH Annual Meeting Abstracts), 106(11):2161.

Sachs, 2014, Induction of Tolerance through Mixed Chimerism, Cold Spring Harb Perspect Med, 4;4:a015529, 19 pages.

Scandling, 2008, Tolerance and Chimerism after Renal and Hematopoietic-Cell Transplantation, N Engl J Med, 358:362-8.

Scandling, 2012, Tolerance and withdrawal of immunosuppressive drugs in patients given kidney and hematopoietic cell transplants, Am J Transplant., 12(5):1133-45.

Scandling, 2015, Chimerism, Graft Survival, and Withdrawal of Immunosuppressive Drugs in HLA Matched and Mismatched Patients After Living Donor Kidney and Hematopoietic Cell Transplantation, American Journal of Transplantation, 15:695-704.

Slavin, 1977, Induction of specific tissue transplantation tolerance using fractionated total lymphoid irradiation in adult mice: long-term survival of allogeneic bone marrow and skin grafts, J. Exp. Med., 146:34-48.

Spohn, 2015, Automated CD34+ cell isolation of peripheral blood stem cell apheresis product, Cytotherapy, 10:1465-71.

Stanford Team Prevent Kidney Transplant Rejection Without Drugs, ScienceDaily, Apr. 24, 2002, pp. 1-3, downloaded from www.sciencedaily.com/releases/2002/04/020424072642.htm.

Strober, 2011, Translational studies in hematopoietic cell transplantation: treatment of hematologic malignancies as a stepping stone to tolerance induction, Semin Immunol., 23(4):273-81.

Sykes, 2001, Mixed Chimerism and Transplant Tolerance, Immunity, 14:417-424.

Szabolcs, 2012, Tolerance after solid organ and hematopoietic cell transplantation, Biol Blood Marrow Transplant, 18(1):S193-200.

Tatekawa, 2006, A novel direct competitive repopulation assay for human hematopoietic stem cells using NOD/SCID mice, Cytotherapy, vol. 8, No. 4, 390-398.

Urbano-Ispizua, 2001, The Number of donor CD3+ cells is the most important factor for graft failure after allogeneic transplantation of CD34+ selected cells from peripheral blood from HLA-identical siblings, Blood,97(2):383-387.

* cited by examiner

METHODS FOR TREATING NON-CANCEROUS DISORDERS USING HEMATOPOIETIC CELLS

CROSS-REFERENCE TO RELATED APPLICATIONS

This application claims the benefit of, and priority to, U.S. Provisional Application No. 62/641,757, filed Mar. 12, 2018, the contents of which are incorporated herein by reference.

FIELD OF THE INVENTION

The invention relates generally to methods of treating non-cancerous disorders by providing donor hematopoietic cells.

BACKGROUND

Millions of people suffer from non-cancerous disorders, including non-cancerous blood cell disorders and other non-cancerous disorders that can be treated by hematopoietic cell transplantation. This diverse group of disorders includes sickle cell disease, thalassemia, enzyme deficiencies, bone marrow failures, and blood clotting disorders that are not due to deficiencies of clotting factors. For example, sickle cell disease, which results from two mutant copies of the hemoglobin beta gene, affects over 4 million people, and another 43 million people have sickle cell trait, a milder disorder caused by a single mutant copy. Although such disorders vary widely in their severity, many lead directly or indirectly to death. For example, the number of deaths each year due to sickle cell disease and thalassemia are approximately 115,000 and 25,000, respectively.

Existing treatments for such non-cancerous disorders are inadequate. An example of a sub-optimal treatment is providing blood transfusions to patients with acute medical problems due to blood cell disorders. Although transfusions replenish the functions that the patient's own blood cells are unable to provide, they do not fix the underlying defect and are thus only temporary solutions. In contrast, bone marrow transplants may provide a permanent cure for disorders such as sickle cell disease, but they carry a high risk of serious complications. Consequently, bone marrow transplants are indicated only for life-threatening conditions. Because safe and effective treatments for non-cancerous blood cell disorders are lacking, millions of people with such disorders continue to lead restricted or shortened lives.

SUMMARY

The invention provides methods of treating qualitative and quantitative disorders that can be treated through hematopoietic cell transplantation by providing compositions that include CD34$^+$ cells and CD3$^+$ cells from a donor. The compositions contain CD34$^+$ cells, which have the capacity to differentiate into a variety of blood cell types, at doses sufficient to populate of the recipient's blood with donor-derived cells. In addition, CD3$^+$ cells facilitate engraftment of CD34$^+$ cells and tolerance of the donor-derived cells by the host immune system. Therefore, the methods allow the recipient's hematopoietic system to be reconstituted to contain a mixture of recipient-derived and donor-derived cells, a state called mixed chimerism. By establishing stable mixed chimerism in the recipient, the methods are able to overcome genetic defects in the recipient's own blood cells while avoiding problems caused by eliminating such cells entirely.

The methods are useful for treatment of non-cancerous disorders, such as non-cancerous blood cell disorders. Non-cancerous blood cell disorders include hemoglobin disorders, such as sickle cell disease and thalassemia, non-factor-based blood clotting disorders, such as thrombocytopenia, bone marrow failures, and other disorders of the hematopoietic system. The methods are also useful for treatment of disorders that primarily affect other organ systems but can be ameliorated by increased or altered function of hematopoietic cells. For example, the methods are useful for treating neurodegenerative diseases such as Friedreich's ataxia (FA) and multiple sclerosis, and enzyme deficiencies, such as lysosomal storage diseases.

In an aspect, the invention provides methods of treating a non-cancerous disorder, including non-cancerous blood cell disorders and other non-cancerous disorders that can be treated by hematopoietic cell transplantation, in a subject that has not and will not receive a solid organ transplant. The methods include providing a cellular product comprising CD34$^+$ cells and CD3$^+$ cells derived from a donor.

The disorder may be associated with aberrant activity of a hematopoietic cell. The disorder may be associated with sickle cell disease or thalassemia. The disorder may be agranulocytosis, anemia, aplasia (e.g., aplastic anemia), a blood clotting disorder that is not due to deficiency of a blood clotting factor, bone marrow failure, cerebral adrenoleukodystrophy, chronic granulomatous disease, cytopenia, Gaucher's disease, hemochromatosis, hemoglobin disorders, Hurler syndrome, leukodystrophy, metachromatic leukodystrophy, myelodysplastic syndrome, severe combined immunodeficiency, Shwachman-Diamond syndrome, sickle cell disease, sickle cell trait, thalassemia (e.g., alpha-thalassemia and beta-thalassemia), and Wiskott-Aldrich syndrome. The disorder may be a non-blood cell disorder that can be mitigated or improved by the function of a hematopoietic cell. For example, the disorder may be ataxia, e.g., Friedreich's ataxia, dyskeratosis congenita, Hurler syndrome, or leukodystrophy.

The CD34$^+$ cells and the CD3$^+$ cells in the cellular product may be HLA-matched to the subject. The CD34$^+$ cells and the CD3$^+$ cells in the cellular product may be matched to the subject at six, eight, ten, or twelve HLA alleles. The CD34$^+$ cells and the CD3$^+$ cells in the cellular product may be matched to the subject at all six alleles of HLA-A, HLA-B, and HLA-DR. The CD34$^+$ cells and the CD3$^+$ cells in the cellular product may be HLA-mismatched to the subject. The CD34$^+$ cells and the CD3$^+$ cells in the cellular product may be mismatched to the subject at one, two, three, four, five, or six alleles of HLA-A, HLA-B, and HLA-DR.

The cellular product may contain at least $1 \times 10^5$ CD34$^+$ cells/kg recipient weight, at least $2 \times 10^5$ CD34$^+$ cells/kg recipient weight, at least $4 \times 10^5$ CD34$^+$ cells/kg recipient weight, at least $5 \times 10^5$ CD34$^+$ cells/kg recipient weight, at least $1 \times 10^6$ CD34$^+$ cells/kg recipient weight, at least $2 \times 10^6$ CD34$^+$ cells/kg recipient weight, at least $4 \times 10^6$ CD34$^+$ cells/kg recipient weight, at least $5 \times 10^6$ CD34$^+$ cells/kg recipient weight, at least $1 \times 10^7$ CD34$^+$ cells/kg recipient weight, at least $2 \times 10^7$ CD34$^+$ cells/kg recipient weight, at least $4 \times 10^7$ CD34$^+$ cells/kg recipient weight, at least $1 \times 10^8$ CD34$^+$ cells/kg recipient weight, at least $2 \times 10^8$ CD34$^+$ cells/kg recipient weight, at least $4 \times 10^5$ CD34$^+$ cells/kg recipient weight, or at least $5 \times 10^8$ CD34$^+$ cells/kg recipient weight. The cellular product may contain at least $1 \times 10^5$ CD3+ cells/kg recipient weight, at least 2×10⁵ CD3+ cells/kg recipient weight, at least 4×10⁵ CD3+ cells/kg recipient weight, at least 5×10⁵ CD3+ cells/kg recipient weight, at least 1×10⁶ CD3+ cells/kg recipient weight, at least 2×10⁶ CD3+ cells/kg recipient weight, at least 4×10⁶ CD3+ cells/kg recipient weight, at least 5×10⁶ CD3+ cells/kg recipient weight, at least 1×10⁷ CD3+ cells/kg recipient weight, at least 2×10⁷ CD3+ cells/kg recipient weight, at least 4×10⁷ CD3+ cells/kg recipient weight, at least 1×10⁸ CD3+ cells/kg recipient weight, at least 2×10⁸ CD3+ cells/kg recipient weight, at least 4×10⁵ CD3+ cells/kg recipient weight, or at least 5×10⁸ CD3+ cells/kg recipient weight. The cellular product may contain about 1×10⁵ CD3+ cells/kg recipient weight, about 2×10⁵ CD3+ cells/kg recipient weight, about 4×10⁵ CD3+ cells/kg recipient weight, about 5×10⁵ CD3+ cells/kg recipient weight, about 1×10⁶ CD3+ cells/kg recipient weight, about 2×10⁶ CD3+ cells/kg recipient weight, about 4×10⁶ CD3+ cells/kg recipient weight, about 5×10⁶ CD3+ cells/kg recipient weight, about 1×10⁷ CD3+ cells/kg recipient weight, about 2×10⁷ CD3+ cells/kg recipient weight, about 4×10⁷ CD3+ cells/kg recipient weight, about 1×10⁸ CD3+ cells/kg recipient weight, about 2×10⁸ CD3+ cells/kg recipient weight, about 4×10⁵ CD3+ cells/kg recipient weight, or about 5×10⁸ CD3+ cells/kg recipient weight. The cellar product may contain at least 1×10⁵ CD34+ cells/kg recipient weight and at least 1×10⁵ CD3+ cells/kg recipient weight, at least 1×10⁶ CD34+ cells/kg recipient weight and at least 1×10⁶ CD3+ cells/kg recipient weight, or at least 4×10⁶ CD34+ cells/kg recipient weight and about 1×10⁸ CD3+ cells/kg recipient weight.

The CD34+ cells and the CD3+ cells may be from a single apheresis product. The CD34+cells and the CD3+ cells may be from multiple apheresis products. The CD34+ cells may be from one portion of an apheresis product, and the CD3+ cells may be from another portion of the apheresis product. The CD34+ cells may be from a portion of an apheresis product that is enriched for CD34+ cells. The CD3+ cells may be from a portion of an apheresis product that is not purified. The CD34+ cells and the CD3+ cells may be from bone marrow.

The CD34+ cells and the CD3+ cells may be provided in separate containers. The CD34+ cells and the CD3+ cells may be provided as a mixture in a common container.

The cellular product may be provided in frozen form. The cellular product may contain one or more cryoprotectants. The cryoprotectant may be DMSO or dextran having an average molecular weight of 40 kDa. The cellular product may have a substantially neutral pH. The cellular product may have pH between 6.0 and 8.0.

The cellular product may be provided in an inpatient procedure. The cellular product may be provided in an outpatient procedure. The cellular product may be provided by infusion.

The donor and subject may be related. The donor and subject may be unrelated. The donor may have been alive at the time of donation, or the donor may have been deceased at the time of donation.

In another aspect, the invention provides methods of treating a non-cancerous disorder in a subject that has not and will not receive a solid organ transplant by providing a cellular product comprising CD34+ cells and CD8+/alpha beta TCR⁻⁰ facilitating cells derived from a donor.

The facilitating cells may have additional phenotypic characteristics. For example, the facilitating cells may be CD56$^{bright}$, cD56$^{dim/neg}$, gamma delta TCR⁻, B220+, CD3 epsilon+, CD3 epsilon⁻, CD19+, CD19⁻, CD11c+, CD11c−, CD11b+, CD11b⁻, CD52+, CD52⁻, or any practicable combination thereof. Other markers that may be present or absent on the facilitating cells include CXCR4, CD123, HLADR, NKp30, NKp44, NKp46, CD162, CD11a, CD62L, and FoxP3.

The facilitating cells may include a mixed population of which at least a certain fraction has the specified phenotype. For example, at least 10%, at least 20%, at least 30%, at least 40%, at least 50%, at least 60%, at least 70%, at least 80%, or at least 00% of the facilitating cells may have the specified phenotype.

The cellular product may contain at least 1×10⁵ CD34+ cells/kg recipient weight, at least 2×10⁵ CD34+ cells/kg recipient weight, at least 4×10⁵ CD34+ cells/kg recipient weight, at least 5×10⁵ CD34+ cells/kg recipient weight, at least 1×10⁶ CD34+ cells/kg recipient weight, at least 2×10⁶ CD34+ cells/kg recipient weight, at least 4×10⁶ CD34+ cells/kg recipient weight, at least 5×10⁶ CD34+ cells/kg recipient weight, at least 1×10⁷ CD34+ cells/kg recipient weight, at least 2×10⁷ CD34+ cells/kg recipient weight, at least 4×10⁷ CD34+ cells/kg recipient weight, at least 1×10⁸ CD34+ cells/kg recipient weight, at least 2×10⁸ CD34+ cells/kg recipient weight, at least 4×10⁵ CD34+ cells/kg recipient weight, or at least 5×10⁸ CD34+ cells/kg recipient weight. The cellular product may contain at least 1×10⁵ facilitating cells/kg recipient weight, at least 2×10⁵ facilitating cells/kg recipient weight, at least 4×10⁵ facilitating cells/kg recipient weight, at least 5×10⁵ facilitating cells/kg recipient weight, at least 1×10⁶ facilitating cells/kg recipient weight, at least 2×10⁶ facilitating cells/kg recipient weight, at least 4×10⁶ facilitating cells/kg recipient weight, at least 5×10⁶ facilitating cells/kg recipient weight, at least 1×10⁷ facilitating cells/kg recipient weight, at least 2×10⁷ facilitating cells/kg recipient weight, at least 4×10⁷ facilitating cells/kg recipient weight, at least 1×10⁸ facilitating cells/kg recipient weight, at least 2×10⁸ facilitating cells/kg recipient weight, at least 4×10⁵ facilitating cells/kg recipient weight, or at least 5×10⁸ facilitating cells/kg recipient weight.

The cellular product may also contain CD34+ cells. The cellular product may contain at least 1×10⁵ CD3+ cells/kg recipient weight, at least 2×10⁵ CD3+ cells/kg recipient weight, at least 4×10⁵ CD3+ cells/kg recipient weight, at least 5×10⁵ CD3+ cells/kg recipient weight, at least 1×10⁶ CD3+ cells/kg recipient weight, at least 2×10⁶ CD3+ cells/kg recipient weight, at least 4×10⁶ CD3+ cells/kg recipient weight, at least 5×10⁶ CD3+ cells/kg recipient weight, at least 1×10⁷ CD3+ cells/kg recipient weight, at least 2×10⁷ CD3+ cells/kg recipient weight, at least 4×10⁷ CD3+ cells/kg recipient weight, at least 1×10⁸ CD3+ cells/kg recipient weight, at least 2×10⁸ CD3+ cells/kg recipient weight, at least 4×10⁵ CD3+ cells/kg recipient weight, or at least 5×10⁸ CD3+ cells/kg recipient weight. The cellular product may contain about 1×10⁵ CD3+ cells/kg recipient weight, about 2×10⁵ CD3+ cells/kg recipient weight, about 4×10⁵ CD3+ cells/kg recipient weight, about 5×10⁵ CD3+ cells/kg recipient weight, about 1×10⁶ CD3+ cells/kg recipient weight, about 2×10⁶ CD3+ cells/kg recipient weight, about 4×10⁶ CD3+ cells/kg recipient weight, about 5×10⁶ CD3+ cells/kg recipient weight, about 1×10⁷ CD3+ cells/kg recipient weight, about 2×10⁷ CD3+ cells/kg recipient weight, about 4×10⁷ CD3+ cells/kg recipient weight, about 1×10⁸ CD3+ cells/kg recipient weight, about 2×10⁸ CD3+ cells/kg recipient weight, about 4×10⁵ CD3+ cells/kg recipient weight, or about 5×10⁸ CD3+ cells/kg recipient weight.

The disorder may be associated with aberrant activity of a hematopoietic cell, such as any of those described above.

The CD34+ cells, the facilitating cells, and, if present, the CD3+ cells in the cellular product may be HLA-matched to the subject. The cells in the cellular product may be matched to the subject at six, eight, ten, or twelve HLA alleles. The cells in the cellular product may be matched to the subject at all six alleles of HLA-A, HLA-B, and HLA-DR. The cells in the cellular product may be HLA-mismatched to the subject. The cells in the cellular product may be mismatched to the subject at one, two, three, four, five, or six alleles of HLA-A, HLA-B, and HLA-DR.

The $CD34^+$ cells and the facilitating cells may be provided in separate containers. The $CD34^+$ cells and the facilitating cells may be provided as a mixture in a common container.

The cellular product may be provided in frozen form, as described above.

The cellular product may be provided in an inpatient procedure. The cellular product may be provided in an outpatient procedure. The cellular product may be provided by infusion.

The donor and subject may be related. The donor and subject may be unrelated. The donor may have been alive at the time of donation, or the donor may have been deceased at the time of donation.

DETAILED DESCRIPTION

The invention provides methods of treating non-cancerous disorders by providing compositions that promote establishment of stable mixed chimerism in the recipient. The compositions include two populations of donor cells that allow development of mature donor-derived blood cells. At the same time, the donor cells do not prevent continued development of recipient-derived blood cells, nor do they mount an immune response to recipient tissue. Consequently, the methods are useful for compensating for functional defects or quantitative deficiencies in a recipient's blood cells without requiring complete ablation of the recipient's hematopoietic system.

A healthy adult human produces up to $10^{12}$ new blood cells per day. All blood cells are derived from hematopoietic stem cells (HSCs), multipotent cells that can differentiate into various specialized cells and also reproduce to generate new HSCs. HSCs that differentiate form either lymphoid progenitors or myeloid progenitors. Lymphoid progenitors give rise to lymphocytes and natural killer cells. Myeloid progenitors produce cells of the myeloid and erythroid lineages, such as erythrocytes, platelets, basophils, neutrophils, eosinophils, monocytes, macrophages, and antigen-presenting cells, such as dendritic cells. In adults, most hematopoietic development occurs in the bone marrow, although maturation and activation of some lymphoid cells occurs in the spleen, thymus, and lymph nodes.

In the methods of the invention, the two populations of cells allow donor HSCs to develop into mature blood cells in the recipient's body. One population includes $CD34^+$ cells. CD34 is a cell surface marker that is expressed in HSCs and their immediate descendants, multipotent progenitor cells, which have not committed to either the myeloid or lymphoid lineage. Consequently, CD34 expression is a useful measure for identifying populations of cells that contain HSCs. The other population includes $CD3^+$ cells. CD3 comprises a group of polypeptides that interact with the two polypeptide chains of the T cell receptor to form the T cell receptor complex. The CD3 complex includes a gamma chain, delta chain, and two epsilon chains. CD3 is expressed on the surface of mature T cells and is thus useful as a marker for T cells.

As indicated above, the methods of the invention are useful for establishing mixed chimerism in a recipient. Mixed chimerism refers to a state in which a recipient's hematopoietic system includes both donor-derived and recipient-derived cells, whereas full or complete chimerism occurs when the recipient's hematopoietic system is composed entirely of donor-derived cells. Mixed chimerism is advantageous over complete chimerism because recipients with mixed chimerism are at lower risk of graft-versus-host disease (GVHD), immunodeficiency, and infection.

It is recognized in the art that compositions containing $CD34^+$ cells and $CD3^+$ cells derived from a donor are useful for promoting tolerance of solid organ transplants. However, the present invention provides methods of using compositions containing donor-derived $CD34^+$ cells and $CD3^+$ cells to treat a variety of non-cancerous conditions in the absence of solid organ transplantation.

Disorders, Diseases, and Conditions

The methods are useful for treating any non-cancerous disease, disorder, or condition in which donor blood cells are of therapeutic benefit. The disease, disorder, or condition may be any qualitative or quantitative disorder that can be treated by hematopoietic cell transplantation. One group of disorders that can be treated in methods of the invention includes blood cell disorders, i.e., disorders in which HSC-derived cells have functional defects. However, the methods are also useful for treating disorders of other organ systems that can be ameliorated by providing donor-derived blood cells.

Given the diversity of cell types that descend from HSCs, the group of disorders associated with defective function of HSC-derived cells is large and diverse.

Bone marrow failure syndromes (BMF) include a group of inherited or acquired diseases. These diseases are disorders of the hematopoietic stem and progenitor cells (HSC) that can involve one or more of the major blood cell lines [erythroid for red blood cells (RBC), myeloid for white blood cells (WBC), and megakaryocytic for platelets]. Lymphocytic cell lines (T-cells and B-cells), which are involved in lymphoproliferative disorders, are usually spared in BMF.

The inherited BMF include rare disorders such as Fanconi anemia, dykeratosis congenita, Shwachman-Diamond syndrome, Diamond-Blackfan anemia, congenital neutropenia, amegakaryocytic thrombocytopenia, thrombocytopenia absent radii syndrome, and other genetic disorders. The acquired BMF include acquired aplastic anemia (AA), the myelodysplastic syndromes (MDS), paroxysmal nocturnal hemoglobinuria (PNH), and large granular lymphocytic leukemia.

Persons with BMF present with low blood counts. Anemia, i.e., abnormally low blood hemoglobin content, can present as rapidly or slowly progressive weakness, fatigue, and symptoms of vascular insufficiency. Thrombocytopenia, i.e., abnormally low blood platelet count, can predispose patients to spontaneous bleeding and "easy" bruising. Neutropenia, i.e., abnormally low blood neutrophil count, places the patient at risk for serious and life-threatening infections. Weakness, bruising, and fever usually prompt affected individuals to seek medical attention. Because low blood counts and their associated symptoms can develop slowly, months or years may elapse between BMF onset and the affected person seeking help.

Many other disorders associated with abnormal erythrocyte function are known.

Hemoglobinopathies are genetic defects that result in abnormal hemoglobin structure and function. Hemoglobinopathies, such as sickle cell disease, arise from mutations in one of the globin chains of hemoglobin. It is estimated that 420 million people carry a mutation that causes hemoglobinopathy. Sickle cell disease is associated with a variety of acute and chronic complications, including acute papillary necrosis, anemia, aplastic crisis, avascular necrosis, chronic kidney failure, dactylitis, gallstones, hemolytic crisis, impaired immune reaction, infection, intrauterine growth retardation, osteomyelitis, pre-eclampsia, priapism, pulmonary hypertension, sequestration crisis, spontaneous abortion, stroke, swelling of the hands or feet, ulcers, vaso-occlusive crisis, and vision problems.

Thalassemias result from underproduction of normal globin proteins. Underproduction may be caused by mutations in other genes that regulate globin expression. Altered expression of HBA1 and HBA2 leads to alpha-thalassemia, whereas beta-thalassemia is due to mutations in HBB. Thalassemia affects about 280 million people worldwide, with over 400,000 having severe disease. Thalassemia may be accompanied by anemia, bone problems, dark urine, enlarged spleen, fatigue, pale or yellowish skin, or slow growth in children.

Methemoglobinemia is a condition that arises from elevated levels of hemoglobin that contains the ferric ($Fe^{3+}$) form of iron. Due to the altered affinity of binding of oxygen to ferric iron, the ability of erythrocytes to release oxygen to tissues is impaired. Methemoglobinemia may be accompanied by coma, cyanosis, dizziness, exercise intolerance, fatigue, headache, loss of hairlines, mental status changes, seizures, or shortness of breath.

Anemia is a decrease in the number of red blood cells or their ability to carry oxygen. Anemia may be due to a hemoglobinopathy or thalassemia. Anemia may be associated with abnormal stool color, angina, cold skin, dizziness, enlarged spleen, fainting, fatigue, heart attack, heart palpitations, low blood pressure, muscle weakness, rapid heart rate chest pain, shortness of breath, skin discoloration, or yellow eyes. Anemia may be due to a genetic disorder, such as abetalipoproteinemia, hereditary spherocytosis, hereditary elliptocytosis, or an enzyme deficiency, such as a deficiency of pyruvate kinase, hexokinase, glucose-6-phosphate dehydrogenase, and glutathione synthetase. Anemia may also be due to blood loss, fluid overload, intestinal inflammation, infection, or autoimmune disease, such as lupus or Evans' syndrome.

Aplastic anemia is a subcategory of anemia in which damages to HSCs prevents restoration of red blood cells. Examples of aplastic anemia include Fanconi anemia, Diamond-Blackfan anemia, and pure red cell aplasia.

Acquired AA is a relatively uncommon and heterogeneous disorder, in general, but a common cause of BMF, in particular. AA is defined as pancytopenia with a hypocellular bone marrow (BM) in the absence of an abnormal infiltrate or marrow fibrosis. The "empty" marrow on histology of AA is characteristic and a prerequisite for the diagnosis. Increased reticulin staining, dysplastic megakaryocytes, and blasts are not seen in AA, as they are in MDS (Bennett & Orazi, 2009). To diagnose AA, at least two of the following blood criteria also known as the Camitta Criteria must exist (Camitta et al, 1975): hemoglobin concentration <10 g/dL (normal 14-17 g/dL), platelet count <50×103/mcL (normal 140-450×103/mcL), and neutrophil count <1.5×103/mcL (normal 1.5-8.0×103/mcL).

The majority (70-80%) of acquired AA cases are idiopathic (Marsh et al, 2009). The remainder may be associated with disorders such as PNH, vitamin B12 deficiency, folate deficiency, medication reactions, pregnancy, systemic lupus erythematosus, chronic viral hepatitis, benzene exposure, human immunodeficiency virus (HIV) infection, or parvovirus B19 infection. The incidence is 2-3 cases per million per year in Europe, and presumably in the United States (US) but higher in East Asia possibly due to environmental exposures (Montane et al, 2008). The majority of AA cases are considered severe or very severe in nature. There is a biphasic age distribution, with peaks at 10-25 years and over 60 years. The severity of acquire AA may be categorized on the following criteria:

Non-severe AA (NSAA)

AA not fulfilling the criteria for SAA or VSAA

Severe AA (SAA)

BM cellularity <25% or 25-50% with <30% residual hematopoietic cells, and

At least two of the following:

Neutrophil count <0.5×103/mcL

Platelet count <20×103/mcL

Reticulocyte count <20×103/mcL

Very Severe AA (VSAA)

Same as for SAA but neutrophil count <0.2×103/mcL

Myelodysplastic syndromes (MDS) make up another subcategory of anemia in which abnormal (dysplastic) cells are produced. The MDS are suspected in the presence of peripheral blood cytopenias (i.e., anemia, thrombocytopenia, and leukopenia), dysplasia, circulating blasts, or MDS-associated cytogenic abnormalities. Cytopenias are defined as values lower than standard lab hematology levels, adjusting for age, sex, ethnic, and altitude norms (Greenberg et al, 2016). Unlike AA, MDS represent myeloid clonal hemopathies with a relatively heterogeneous spectrum of initial presentation. The major clinical problems in MDS are morbidities caused by cytopenias and the potential for MDS to evolve into AML.

The diagnosis of MDS requires careful blood and bone marrow morphologic review and correlation with the patient's clinical features, because several medications and viral infections (including HIV infection) can cause morphologic changes in marrow cells that are similar to MDS (Kaloutsi et al, 1994). Recommended minimum diagnostic criteria include two prerequisites: 1) stable cytopenia and 2) the exclusion of other potential causes for dysplasia, cytopenia, or both. Stable cytopenia requires 6 months of stable blood counts unless accompanied by a specific MDS karyotype or bilineage dysplasia, in which case only 2 months of stable cytopenia are needed. In addition, the diagnosis of MDS requires at least one of three MDS-related and decisive criteria (Arber et al, 2016): (1) dysplasia (≥10% in one or more of the three major bone marrow lineages), (2) a blast cell count of 5% to 19%, and (3) a specific MDS-associated karyotype [e.g., del(5q), del(20q), +8, or −7/del(7q)].

The current World Health Organization (WHO) classification guidelines for MDS identifies six entities of MDS with MDS, with excess blasts (MDS-EB) divided into two sub entities. MDS-EB in transformation having 20% to 29% blasts and AML having >30% blasts >30% is likely a distinction without a difference. WHO classification guidelines for MDS are provided in Table 1.

TABLE 1

| MDS Subtype | Blood Findings | Bone Marrow Findings |
| --- | --- | --- |
| MDS with single lineage dysplasia (MDS-SLD) | Single or bicytopenia | Dysplasia in blasts ≥10% of one cell line, <5% |
| MDS with ring sideroblasts (MDS-RS) | Anemia, no blasts | ≥15% of erythroid precursors with ring sideroblasts or ≥5% ring sideroblasts if SF3B1 mutation present |
| MDS with multilineage dysplasia (MDS-MLD) | Cytopenia(s), <1 × 109/L monocytes | Dysplasia in ≥10% of cells in ≥2 hematopoietic lineages, <15% ring sideroblasts or ≥5% ring sideroblasts if SF3B1 mutation present, <5% blasts |
| MDS with excess blasts-1 (MDS-EB-1) | Cytopenia(s), ≤2%-4% blasts, <1 × 109/L monocytes | Unilineage or multilineage dysplasia, 5%-9% blasts, no Auer rods |
| MDS with excess blasts-2 (MDS-EB-2) | Cytopenia(s), 5%-19% blasts, <1 × 109/L monocytes | Unilineage or multilineage dysplasia, 10%-19% blasts, ± Auer rods |
| MDS unclassifiable (MDS-U) | Cytopenia(s), ±1% blasts on at least 2 occasions | Unilineage dysplasia or no dysplasia but characteristic MDS cytogenetics, <5% blasts |
| MDS with isolated del(5q) | Anemia, platelet count normal or increased | Unilineage erythroid dysplasia, isolated del(5q), <5% blasts ± one other abnormality except −7/del(7q) |

Several disorders associated with decreased or aberrant function of cells in the myeloid lineage have been described.

Neutropenia is a deficiency of neutrophils in the blood. Chronic neutropenia may be due to aplastic anemia, glycogen storage disease, Cohen syndrome, congenital immunological disorder, Barth syndrome, vitamin B12 deficiency, Pearson syndrome, Pudlak syndrome, or Shwachman-Diamond syndrome. Transient neutropenia may be due to an infection or a medication.

Agranulocytosis is a deficiency of one or more types of granulocytes. Thus, patients with agranulocytosis may have low levels of neutrophils, eosinophils, basophils, mast cells, or some combination thereof.

Other blood cell disorders result from defective platelet levels or function.

Glanzmann's thrombasthenia is a bleeding disorder in which platelets contain insufficient or defective glycoprotein IIb/IIIa. It may be hereditary or acquired as an autoimmune disorder.

Thrombocytopenia is characterized by low levels of platelets in the blood. Thrombocytopenia may be due to a genetic deficiency in platelet development, such as Alport syndrome, Bernard-Soulier syndrome, congenital amegakaryocytic thrombocytopenia, Fanconi anemia, Grey platelet syndrome, May-Hegglin anomaly, thrombocytopenia absent radius syndrome, or Wiskott-Aldrich syndrome. Thrombocytopenia may be caused by increased platelet destruction, for example, by antiphospholipid syndrome, Dengue fever, disseminated intravascular coagulation, Gaucher's disease, hemolytic-uremic syndrome, hypersplenism, immune thrombocytopenic purpura, lupus, neonatal alloimmune thrombocytopenia, paroxysmal nocturnal hemoglobinuria, post-transfusion purpura, thrombotic thrombocytopenic purpura, or Zika virus. Thrombocytopenia may be a side effect of a medication.

The immune system comprises cells of lymphoid lineage, and many disorders of the immune systems are known.

One group of immune disorders includes autoimmune disorders. Autoimmune disorders include hemolytic anemia, Goodpasture's syndrome, Graves disease, lupus, Lyme disease, multiple sclerosis (although it is thought to be an immune-mediated process), pernicious anemia, rheumatoid arthritis, scleroderma, myopathy, type one diabetes, and vasculitis.

Another group of immune disorders includes immunodeficiencies. Immunodeficiencies include AIDS, ataxia-telangiectasia, autoimmune lymphoproliferative syndrome (ALPS), chronic granulomatous disease (CGD), common variable immunodeficiency (CVID), DiGeorge syndrome, hyper IgM syndrome, hyperimmunoglobulin E syndrome (aka Job's Syndrome), leukocyte adhesion deficiency (LAD), NF-KB Essential Modifier (NEMO) mutations, selective immunoglobulin A deficiency, Severe combined immunodeficiency (SCID), Wiskott-Aldrich syndrome (WAS), X-linked agammaglobulinemia (XLA; aka Bruton type agammaglobulinemia), and X-linked lymphoproliferative disease (XLP).

Chronic granulomatous disease is a group of hereditary diseases in which immune cells are deficient in formation of reactive oxygen compounds, such as the superoxide radical. Reactive oxygen compounds are important for killing ingested pathogens, and CGD patients are prone to recurrent infections, such as pneumonia, abscesses, septic arthritis, osteomyelitis, bacteremia, and fungemia. CGD is usually caused by a mutation in PHOX, CYBA, or NCF1.

Gaucher's disease is a genetic disorder that causes anemia low platelet count. Gaucher's disease results from a deficiency in glucocerebrosidase, and the sphigolipid glucocerebroside accumulates in the cells and certain organs of patients. The disease is also associated with hepatomegaly, splenomegaly, anemia, neutropenia, leukopenia, and thrombocytopenia. Gaucher's is the most common lysosomal storage disease.

Other blood cell disorders include asplenia, hemochromatosis, hemophagocytic lymphohistiocytosis, hypersplenism, monoclonal gammopathy, and Tempi syndrome.

HSC transplantation is effective for treating a variety of disorders that result from impaired function of organ systems other than blood cells of the erythroid, myeloid, and lymphoid lineages. Therefore, the methods of the invention are useful for treating such disorders.

Several neuronal demyelination disorders may be treated by the methods of the invention. Friedreich's ataxia is a neurodegenerative disease in which the spinal cord becomes thinner and neurons lose some of their myelin sheath. Friedreich's ataxia is caused by an autosomal recessive mutation that leads to decreased expression of the mitochondrial protein frataxin. In dorsal root ganglia of Friedreich's ataxia patients, dying neurons are accompanied by proliferation of glial satellite cells and high levels of monocytes. See Koeppen et al., Dorsal root ganglia in Friedreich ataxia: satellite cell proliferation and inflammation, Acta Neuropathologica Communications (2016) 4:46; DOI 10.1186/s40478-016-0288-5, incorporated herein by reference. Without wishing to be bound by theory, neuronal destruction may result from inflammatory infiltration, and providing healthy donor blood cells may mitigate such inflammatory destruction.

Other demyelinating diseases that may be treated by the methods of the invention include multiple sclerosis and leukodystrophies, such as metachromatic leukodystrophy, Krabbe disease, Canavan disease, X-linked adrenoleukodystrophy, and Alexander disease. Gene therapy using autologous HSCs containing lentiviral vectors to transfer the disease gene has been effective for treatment of X-linked adrenoleukodystrophy, metachromatic leukodystrophy, and Krabbe Disease. Thus, providing donor cells according to the methods of the invention may be useful for treating such diseases. See also Bakhuraysah et al., Hematopoietic stem cell transplantation for multiple sclerosis: is it a clinical reality? Stem Cell Res Ther. 2016; 7:12, doi: 10.1186/s13287-015-0272-1, the contents of which are incorporated herein by reference.

The methods may also be used to treat lysosomal storage disorders, such as alpha-mannosidosis, aspartylglucosaminuria, beta-mannosidosis ceramidase deficiencies, such as Farber disease and Krabbe disease, cholesteryl ester storage disease fucosidosis, galactosialidosis, gangliosidoses, such as Fabry disease (alpha-galactosidase A), Schindler disease (alpha-galactosidase B), and GM1 gangliosidosis, GM2 gangliosidosis, Sandhoff disease, Tay-Sachs disease, Gaucher's disease, lipidoses, such as Niemann-Pick disease, neuronal ceroid lipofuscinoses, lysosomal acid lipase deficiency, lysosomal transport diseases, such as cystinosis, pycnodysostosis, salla disease, infantile free sialic acid storage disease, metachromatic leukodystrophy, mucolipidosis, mucopolysaccharidoses, such as Hurler syndrome, Scheie syndrome, Hurler-Scheie syndrome, Hunter syndrome, Sanfilippo syndrome, Morquio, Maroteaux-Lamy syndrome, Sly syndrome, hyaluronidase deficiency, multiple sulfatase deficiency, Niemann-Pick disease, saposin B deficiency, sphingolipidoses, sulfatidosis, type II Pompe disease, type IIb Danon disease, and Wolman disease. For example, Hurler syndrome is a genetic deficiency of alpha-L iduronidase, which degrades mucopolysaccharides in lysosomes, that is usually fatal by the teenage years. HSC transplantation can extend the life of Hurler syndrome patients. See Aldenhoven et al., Quality of life of Hurler syndrome patients after successful hematopoietic stem cell transplantation, Blood Adv. 2017 Nov. 7; 1(24):2236-2242. doi: 10.1182/bloodadvances.2017011387, incorporated herein by reference.

Cellular Products and Preparation Thereof

The methods of the invention include providing a cellular product that contains CD34$^+$ cells and CD3$^+$ cells from a donor. Each population of cells is provided at a quantity sufficient to promote mixed chimerism in the recipient. Cell quantity may be expressed in terms of number of cells per kg of the recipient's body weight.

For example, the cellular product may contain CD34$^+$ cells at $\geq 1\times 10^4$ cells/kg of body weight, $\geq 2\times 10^4$ cells/kg of body weight, $\geq 4\times 10^4$ cells/kg of body weight, $\geq 5\times 10^4$ cells/kg of body weight, $\geq 1\times 10^5$ cells/kg of body weight, $\geq 2\times 10^5$ cells/kg of body weight, $\geq 4\times 10^5$ cells/kg of body weight, $\geq 5\times 10^5$ cells/kg of body weight, $\geq 1\times 10^6$ cells/kg of body weight, $\geq 2\times 10^6$ cells/kg of body weight, $\geq 4\times 10^6$ cells/kg of body weight, $\geq 5\times 10^6$ cells/kg of body weight, $\geq 1\times 10^7$ cells/kg of body weight, $\geq 2\times 10^7$ cells/kg of body weight, $\geq 4\times 10^7$ cells/kg of body weight, $\geq 5\times 10^7$ cells/kg of body weight, $\geq 1\times 10^8$ cells/kg of body weight, $\geq 2\times 10^8$ cells/kg of body weight, $\geq 4\times 10^8$ cells/kg of body weight, or $\geq 5\times 10^8$ cells/kg of body weight.

The cellular product may contain CD3$^+$ cells at $\geq 1\times 10^4$ cells/kg of body weight, $\geq 2\times 10^4$ cells/kg of body weight, $\geq 4\times 10^4$ cells/kg of body weight, $\geq 5\times 10^4$ cells/kg of body weight, $\geq 1\times 10^5$ cells/kg of body weight, $\geq 2\times 10^5$ cells/kg of body weight, $\geq 4\times 10^5$ cells/kg of body weight, $\geq 5\times 10^5$ cells/kg of body weight, $\geq 1\times 10^6$ cells/kg of body weight, $\geq 2\times 10^6$ cells/kg of body weight, $\geq 4\times 10^6$ cells/kg of body weight, $\geq 5\times 10^6$ cells/kg of body weight, $\geq 1\times 10^7$ cells/kg of body weight, $\geq 2\times 10^7$ cells/kg of body weight, $\geq 4\times 10^7$ cells/kg of body weight, $\geq 5\times 10^7$ cells/kg of body weight, $\geq 1\times 10^8$ cells/kg of body weight, $\geq 2\times 10^8$ cells/kg of body weight, $\geq 4\times 10^8$ cells/kg of body weight, or $\geq 5\times 10^8$ cells/kg of body weight. The cellular product may contain CD3$^+$ cells at about $1\times 10^4$ cells/kg of body weight, about $2\times 10^4$ cells/kg of body weight, about $4\times 10^4$ cells/kg of body weight, about $5\times 10^4$ cells/kg of body weight, about $1\times 10^5$ cells/kg of body weight, about $2\times 10^5$ cells/kg of body weight, about $4\times 10^5$ cells/kg of body weight, about $5\times 10^5$ cells/kg of body weight, about $1\times 10^6$ cells/kg of body weight, about $2\times 10^6$ cells/kg of body weight, about $4\times 10^6$ cells/kg of body weight, about $5\times 10^6$ cells/kg of body weight, about $1\times 10^7$ cells/kg of body weight, about $2\times 10^7$ cells/kg of body weight, about $4\times 10^7$ cells/kg of body weight, about $5\times 10^7$ cells/kg of body weight, about $1\times 10^8$ cells/kg of body weight, about $2\times 10^8$ cells/kg of body weight, about $4\times 10^8$ cells/kg of body weight, or about $5\times 10^8$ cells/kg of body weight.

The cellar product may contain at least $1\times 10^5$ CD34$^+$ cells/kg recipient weight and at least $1\times 10^5$ CD3$^+$ cells/kg recipient weight, at least $1\times 10^6$ CD34$^+$ cells/kg recipient weight and at least $1\times 10^6$ CD3$^+$ cells/kg recipient weight, or at least $4\times 10^6$ CD34$^+$ cells/kg recipient weight and about $1\times 10^8$ CD3$^+$ cells/kg recipient weight.

Facilitating cells are non-stem cells that improve long-term engraftment of stem cells. Facilitating cells and methods of preparing them are known in the art and described in, for example, U.S. Pat. Nos. 5,772,994; 8,632,768; 9,452,184; and 9,678,062 the contents of which are incorporated herein by reference.

Facilitating cells may be characterized based on presence, absence, or level of expression of phenotypic markers. Typically, facilitating cells are CD8$^+$ and alpha beta TCR$^-$. However, alternative or additional markers may be used to characterize facilitating cells. For example and without limitation, facilitating cells may be characterized by the presence, absence, or level of one or more of B220, CD11a, CD11b, CD11c, CD123, CD162, CD19, CD3 epsilon, CD52, CD56, CD62L, CXCR4, FoxP3, gamma delta TCR, HLADR, NKp30, NKp44, and NKp46.

The cellular product may contain facilitating cells at $\geq 1\times 10^4$ cells/kg of body weight, $\geq 2\times 10^4$ cells/kg of body weight, $\geq 4\times 10^4$ cells/kg of body weight, $\geq 5\times 10^4$ cells/kg of body weight, $\geq 1\times 10^5$ cells/kg of body weight, $\geq 2\times 10^5$ cells/kg of body weight, $\geq 4\times 10^5$ cells/kg of body weight, $\geq 5\times 10^5$ cells/kg of body weight, $\geq 1\times 10^6$ cells/kg of body weight, $\geq 2\times 10^6$ cells/kg of body weight, $\geq 4\times 10^6$ cells/kg of body weight, $\geq 5\times 10^6$ cells/kg of body weight, $\geq 1\times 10^7$ cells/kg of body weight, $\geq 2\times 10^7$ cells/kg of body weight, $\geq 4\times 10^7$ cells/kg of body weight, $\geq 5\times 10^7$ cells/kg of body weight, $\geq 1\times 10^8$ cells/kg of body weight, $\geq 2\times 10^8$ cells/kg of body weight, $\geq 4\times 10^8$ cells/kg of body weight, or $\geq 5\times 10^8$ cells/kg of body weight.

The CD34$^+$ cells, CD3$^+$ cells, and/or facilitating may be from the same donor. The CD34$^+$ cells, CD3$^+$ cells and/or facilitating cells may be from different donors. The donor may be the same as the recipient, i.e., autologous. The donor may be different from the recipient, i.e., allogeneic.

The CD34$^+$ cells and CD3$^+$ cells may be provided as a mixture in one or more containers. The CD34$^+$ cells and CD3$^+$ cells may be provided in separate container.

The cellular product may be provided frozen. Consequently, the cellular product may contain a cryoprotectant, such as DMSO, dextran having an average molecular weight of 40 kDa, or calf serum. The cryoprotectant may be present at a defined concentration. For example, the cellular product may contain about 1% DMSO, about 2% DMSO, about 5% DMSO, about 7.5% DMSO, about 10% DMSO, about 12.5% DMSO, about 15% DMSO, or about 20% DMSO. The cellular product may contain about 1% dextran, about 2% dextran, about 5% dextran, about 7.5% dextran, about 10% dextran, about 12.5% dextran, about 15% dextran, or about 20% dextran.

The cellular product may contain other ingredients that facilitate engraftment or mobilization of the cells. For example, the cellular product may contain matrix proteins that support or promote adhesion of the cells, or it may contain complementary cell types, e.g., endothelial cells.

The cellular product can be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, see Cell Therapy: Stem Cell Transplantation, Gene Therapy, and Cellular Immunotherapy, by G. Morstyn & W. Sheridan eds, Cambridge University Press, 1996; and Flematopoietic Stem Cell Therapy, E. D. Ball, J. Lister & P. Law, Churchill Livingstone, 2000.

The cellular product may contain a buffer. The cellular product may be buffer to maintain physiologically compatible pH. For example, the cellular product may be buffered to a neutral pH, such as from about 6.0 to about 8.0.

The donor cells may be HLA-matched or HLA-mismatched to the recipient. Human leukocyte antigens (HLAs), also called major histocompatibility complex (MHC) antigens, are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells.

A key aspect of the HLA gene system is its polymorphism. Each gene exists in different alleles. Allelic gene products differ in one or more amino acids in the alpha and/or beta domain(s). An individual has two alleles of each gene, for a total of twelve alleles among the HLA-A, HLA-B, HLA-C, HLA-DP, HLA-DQ, and HLA-DR genes. An HLA-matched donor may have a match with the recipient at six, eight, ten, or twelve alleles selected from any combination of the HLA-A, HLA-B, HLA-C, HLA-DP, HLA-DQ, and HLA-DR genes. The genes most important for HLA typing are HLA-A, HLA-B, and HLA-DR, so the donor and recipient may be matched at all six alleles of the HLA-A, HLA-B, and HLA-DR genes. An HLA-mismatched donor may have a mismatch at one, two, three, four, five, six, or more alleles among the the HLA-A, HLA-B, HLA-C, HLA-DP, HLA-DQ, and HLA-DR genes. HLA typing may be performed by any method known in the art. Examples of HLA typing methods include serological cytotoxicity, flow cytometry, and DNA typing. Such methods are described in, for example, U.S. Pat. No. 9,561,253, the contents of which are incorporated herein by reference.

The HLA genes are clustered in a super-locus present on chromosome position 6p21. Consequently, the set of alleles present on a single chromosome, i.e., a haplotype, tends to be inherited as a group. Identifying a patient's haplotypes can help predict the probability of finding matching donors and assist in developing a search strategy. Haplotypes vary in how common they are among the general population and in their frequency within different racial and ethnic groups.

CD34$^+$ cells and CD3$^+$ cells may be obtained from living or deceased donors. From deceased donors, CD34$^+$ cells and CD3$^+$ cells may be obtained from bone marrow. From living donors, CD34$^+$ cells and CD3$^+$ cells may be collected by apheresis or obtained from bone marrow. Prior to apheresis, living donors may be treated with a mobilization factor such as G-CSF. Regimens for G-CSF treatment are described in U.S. Pat. No. 9,561,253, the contents of which are incorporated herein by reference. Bone marrow may be extracted from vertebrae, the pelvic bone, femur, or other large bones that contain sufficient marrow.

The cellular product may be prepared by dividing a source of hematopoietic cells, such as an apheresis product or extracted bone marrow, into two fractions and using the two fractions as separate sources of CD34$^+$ cells and CD3$^+$ cells for the cellular product. CD34$^+$ cells may be isolated and purified from one fraction, and CD3$^+$ cells may be isolated and purified from the other fraction.

In a preferred method, an apheresis product is split into two fractions. One fraction is enriched for CD34$^+$ cells, and the enriched CD34$^+$-enriched fraction is used as the source of CD34$^+$ cells in the cellular product. The second fraction is not enriched for a cell population, and it is used as the source of CD34$^+$ cells in the cellular product. For example, CD34$^+$ cells may be enriched in the first fraction by passing the first fraction through an affinity purification column, as described below, and the second fraction may not be passed through a purification column.

CD34$^+$or CD3$^+$ cells may be isolated, enriched, and/or purified from the donor hematopoietic cells by any suitable method. For example, CD34$^+$or CD3$^+$ cells may be isolated and purified by selectively binding a suitable CD34 or CD3 affinity reagent, respectively. The affinity reagent may be an antibody, a full-length antibody, a fragment of an antibody, a naturally occurring antibody, a synthetic antibody, an engineered antibody, a full-length affibody, a fragment of an affibody, a full-length affilin, a fragment of an affilin, a full-length anticalin, a fragment of an anticalin, a full-length avimer, a fragment of an avimer, a full-length DARPin, a fragment of a DARPin, a full-length fynomer, a fragment of a fynomer, a full-length kunitz domain peptide, a fragment of a kunitz domain peptide, a full-length monobody, a fragment of a monobody, a peptide, a polyaminoacid, or the like. The affinity reagent may be directly conjugated to a detection reagent and/or purification reagent. The detection reagent and purification reagent may be the same, or they may be different. For example, the detection reagent and/or purification reagent may be fluorescent, magnetic, or the like. The detection reagent and/or purification reagent may be a magnetic particle for column purification. For example, magnetic column purification may be performed using the Miltenyi system of columns, antibodies, buffers, preparation materials and reagents, etc. known to those of skill in the art. Methods of affinity purification of hematopoietic cells, including CD34$^+$ and CD3$^+$ cells, and analysis of purified populations are described in, for example, U.S. Pat. Nos. 9,561,253; and 9,452,184, the contents of which are incorporated herein by reference.

CD34$^+$ cells and/or CD3$^+$ cells may be frozen. Cells may be frozen prior at any stage in the preparation process. For example, cells may be frozen immediately after an apheresis product or bone marrow is isolated from a donor but prior to separation into fractions, after separation into fractions, after purification or enrichment, etc. Method of freezing, i.e., cryopreserving, cells are known in the art.

CD34$^+$ cells and/or CD3$^+$ cells may be expanded ex vivo. Expansion may occur prior to, or subsequent to, freezing. Expansion may include providing one or more growth factors, and it may include culturing cells in the presence of another cell type, e.g., feeder cells. Methods for expanding hematopoietic cells are described in, for example, U.S. Pat. No. 9,561,253, the contents of which are incorporated herein by reference.

The CD34$^+$ cells and/or CD3$^+$ cells may be genetically modified ex vivo. For example, in autologous transfer of donor cells, a genetic defect may be corrected using gene therapy. Methods of gene therapy are described in, for example, Mali, Delivery systems for gene therapy, Indian J Hum Genet. 2013 January-March; 19(1): 3-8, doi: 10.4103/0971-6866.112870; Gennady Ermak (2015) FRONT MATTER. Emerging Medical Technologies, ISBN: 978-981-4675-80-2, doi.org/10.1142/9789814675826_fmatter; and Bakhuraysah et al., Hematopoietic stem cell transplantation for multiple sclerosis: is it a clinical reality? Stem Cell Res Ther. 2016; 7:12, doi: 10.1186/s13287-015-0272-1, the contents of each of which are incorporated herein by reference.

Providing Cellular Products to a Recipient

The cellular product may be provided by any suitable means according to the methods of the invention. For example and without limitation, the hematopoietic cells may be delivered to the recipient by injection using a needle, catheter, central line or the like. In some cases, the cells may be delivered intravascularly, intravenously, intraarterially, intracranially, intraperitoneally, subcutaneously, intramuscularly, intraorbitally, directly to the bone, or through any source which permits the hematopoietic cells to home to an appropriate site in the recipient such that the hematopoietic cells persist, regenerate and differentiate in the recipient. The cellular product may be provided by infusion. The cellular product may be provided in an inpatient procedure or in an outpatient procedure. An inpatient procedure requires admission to a hospital, and the patient may spend one or more nights in the hospital. An outpatient procedure does not require admission to a hospital and may be performed in a non-hospital setting, such as a clinic, doctor's office, home, or other location.

To facilitate establishment of mixed chimerism in the recipient, the recipient's immune system may be conditioned in conjunction with providing the cellular product. For example, non-myeloablative conditioning may be used. In non-myeloablative conditioning, the recipient is exposed to drugs, antibodies, irradiation, or some combination thereof at a dose that is too low to eradicate all the bone marrow cells. Typically, the conditioning regimen includes treatment with anti-thymocyte globulin (ATG), total lymphoid irradiation, and corticosteroids (e.g. prednisone) for a period of from about 10 to 12 days (e.g. for about 11 days).

The irradiation may be targeted to a particular location of the recipient's body. For example, irradiation may be targeted to a tissue, an organ, a region of the body or the whole body. Irradiation may be targeted to the lymph nodes, the spleen, or the thymus or any other area known to a person of skill in the art. When multiple doses of irradiation are administered, the doses may be targeted to the same location or to different locations. Non-myeloablative conditioning may include the use of a T cell depleting agent, such as a monoclonal antibody or drug, e.g., fludarabine. Regimens for non-myeloablative conditioning are known in the art and are described in, for example, U.S. Pat. No. 9,561,253, the contents of which are incorporated herein by reference.

The methods may include immunosuppressive therapy. Immunosuppressive therapy, or immunosuppression, involves treatment of the graft recipient with agents that diminish the response of the host immune system against the donor cells, which can lead to graft rejection. Primary immunosuppressive agents include calcineurin inhibitors, such as tacrolimus, cyclosporin A. Adjuvant agents are usually combined with a calcineurin inhibitor. Adjuvant agents include steroids, azathioprine, mycophenolic acid (MPA) agents, e.g., mycophenolate mofetil, mTOR inhibitors, e.g., sirolimus, and belatacept. The use of adjuvant agents allows clinicians to achieve adequate immunosuppression while decreasing the dose and toxicity of individual agents. Antibody-based therapy may use monoclonal (e.g., muromonab-CD3) or polyclonal antibodies or anti-CD25 antibodies (e.g., basiliximab, daclizumab). Antibody-based therapy allows for avoidance or dose reduction of calcineurin inhibitors, possibly reducing the risk of nephrotoxicity. Regimens for immunosuppressive therapy are known in the art and are described in, for example, U.S. Pat. No. 9,561,253, the contents of which are incorporated herein by reference.

Immunosuppression may also diminish the response of the donor immune cells against recipient tissue, which can lead to graft-versus-host disease (GVHD). GVHD is a risk for both HLA-matched and—mismatched grafts. GVHD can occur even if the donor and recipient are HLA-matched because the immune system can still recognize other differences between their tissues. GVHD is usually mediated by T cells, which react to foreign peptides presented on the MHC of the host. Significantly, the risk of GVHD is markedly reduced in patients with mixed instead of complete chimerism GVHD may be acute or chronic. Acute GVHD typically occurs in the first 3 months after graft and may involve the skin, intestine, or the liver. Treatment for acute GVHD usually includes high-dose corticosteroids such as prednisone. Chronic GVHD typically occurs after the first 3 months following transplant and is the major source of late treatment-related complications. Chronic GVHD may cause functional disability and require prolonged immunosuppressive therapy.

Immunosuppressive therapy may occur in multiple phases. For example, the immunosuppressive regimen may have an induction phase and a maintenance phase. Induction and maintenance phase strategies may use different medicines at doses adjusted to achieve target therapeutic levels to enhance establishment of mixed chimerism in the recipient.

Immunosuppressive therapy may be withdrawn after stable mixed chimerism has been established in the recipient. The chimeric status of the recipient may be monitored as described below and deemed stable after a certain period, for example, 3 months, 6 months 12 months, 18 months, 24 months, or longer. Thus, immunosuppression may be discontinued for the recipients after a certain period, for example, 3 months, 6 months 12 months, 18 months, 24 months, or longer. Withdrawal of immunosuppressive therapy may include tapering, i.e., progressively reducing the dosage or frequency of treatment.

A determination of whether an individual is a full chimera, mixed chimera, or non-chimera made be made by an analysis of a hematopoietic cell sample from the graft recipient, e.g. peripheral blood, bone marrow, etc. as known in the art. Analysis may be done by any convenient method of typing. Analysis may be performed on hematopoietic cells or a subset thereof, such as all mononuclear cells, T cells, B cells, $CD56^+$ NK cells, and $CD15^+$ neutrophils. Chimerism can be assessed by PCR analysis of microsatellites. For example, commercial kits that distinguish polymorphisms in short terminal repeat lengths of donor and host origin are available. Automated readers provide the percentage of donor type cells based on standard curves from artificial donor and host cell mixtures.

Recipients can be categorized as fully chimeric, mixed chimeric, or non-chimeric based on the fraction of cells that are derived from the donor. For example, recipients can be deemed fully chimeric if they have at least 90%, at least 95%, at least 98%, or at least 99% donor-derived cells. Recipients can be deemed mixed chimeric if they have too few donor-derived cells to be categorized as fully chimeric but a fraction of donor-derived cells that exceeds a certain threshold, such as at least 0.5%, at least 1%, at least 2%, at least 3%, at least 5%, at least 7.5%, at least 10% donor-derived cells. Recipients can be deem non-chimeric if the fraction of donor-derived cells falls below the threshold required to be categorized as mixed chimeric.

The methods of the invention may include providing $CD34^+$ and $CD3^+$ cells to a recipient in conjunction with other therapies that treat the recipient's disease, disorder, or condition. For example, the methods may include providing an additional pharmacological agent, blood transfusion, surgery, or physical therapy. Blood transfusions may include transfusions of whole blood or a fraction of blood, such as plasma, serum, platelets, red blood cells, or another cellular fraction. The additional pharmaceutical agent may be a non-steroidal anti-inflammatory drug (NSAID) (e.g., naproxen, ibuprofen, diclofenac, or aspirin), antibiotic (e.g. penicillin), hydroxyurea, opioid, amino acid (e.g., L-glutamine), chelating agent (e.g., deferoxamine, deferiprone, or deferasirox), antibody (e.g., anti-thymocyte globulin), immunosuppressive therapeutic, steroid, desmopressin, heparin, or Factor Xa inhibitor.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of treating a non-cancerous disorder, the method comprising:
    providing to a subject with a non-cancerous disorder associated with aberrant activity of a hematopoietic cell, performing non-myeloablative conditioning to the subject, said conditioning comprising multiple rounds of total lymphoid irradiation, and wherein the subject has not and will not receive a solid organ transplant; and
    delivering to the subject a cellular product comprising $CD34^+$ cells and $CD3^+$ cells derived from a donor, wherein the cellular product comprises between about $1\times10^8$ and about $5\times10^8$ $CD3^+$ cells/kg of the subject's weight.

2. The method of claim 1, wherein the disorder is selected from the group consisting of agranulocytosis, anemia, aplasia, ataxia, a blood clotting disorder that is not due to deficiency of a blood clotting factor, bone marrow failure, cerebral adrenoleukodystrophy, chronic granulomatous disease, cytopenia, dyskeratosis congenita, Gaucher's disease, hemochromatosis, hemoglobin disorders, Hurler syndrome, leukodystrophy, metachromatic leukodystrophy, mitochondrial neurogastrointestinal encephalomyopathy, myelodysplastic syndrome, severe combined immunodeficiency, Shwachman Diamond syndrome, sickle cell disease, sickle cell trait, thalassemia, and Wiskott-Aldrich syndrome.

3. The method of claim 2, wherein the disorder is aplastic anemia, beta thalassemia, bone marrow failure, chronic granulomatous disease, Gaucher's disease, myelodysplastic syndrome, or sickle cell disease.

4. The method of claim 2, wherein the disorder is thalassemia or ataxia.

5. The method of claim 1, wherein the $CD34^+$ cells and the $CD3^+$ cells are HLA-matched to the subject.

6. The method of claim 1, wherein the $CD34^+$ cells and the $CD3^+$ cells are HLA-mismatched to the subject.

7. The method of claim 1, wherein the $CD34^+$ cells and the $CD3^+$ cells are from a single apheresis product.

8. The method of claim 1, wherein the $CD34^+$ cells and the $CD3^+$ cells are from multiple apheresis products.

9. The method of claim 1, wherein:
    the $CD34^+$ cells are from a first portion of at least one apheresis product; and
    the $CD3^+$ cells are from a second portion of the least one apheresis product.

10. The method of claim 9, wherein the first portion of the at least one apheresis product is enriched for $CD34^+$ cells.

11. The method of claim 9, wherein the second portion of the at least one apheresis product is not purified.

12. The method of claim 1, wherein the $CD34^+$ cells and the $CD3^+$ cells are provided in separate containers.

13. The method of claim 1, wherein the $CD34^+$ cells and the $CD3^+$ cells are provided as a mixture in a common container.

14. The method of claim 1, wherein the cellular product is cryopreserved before the delivering step.

15. The method of claim 14, wherein the cellular product further comprises a cryoprotectant selected from the group consisting of DMSO and dextran having an average molecular weight of 40 kDa.

16. The method of claim 1, wherein the subject is related to the donor.

17. The method of claim 1, wherein the donor was deceased when the CD34$^+$cells and the CD3$^+$cells were donated.

18. The method of claim 17, wherein the CD34$^+$cells and the CD3$^+$cells are frog bone marrow.

19. The method of claim 1, wherein the step of delivering the cellular product is an inpatient procedure.

20. The method of claim 19, wherein the step of delivering the cellular product comprises delivering the cellular product to the subject by infusion.

21. The method of claim 1, wherein the step of delivering the cellular product is an outpatient procedure.

22. The method of claim 21, wherein the step of delivering the cellular product comprises delivering the cellular product to the subject by infusion.

* * * * *